US005462575A

United States Patent [19]
Del Corso

[11] Patent Number: 5,462,575
[45] Date of Patent: Oct. 31, 1995

[54] CO-CR-MO POWDER METALLURGY ARTICLES AND PROCESS FOR THEIR MANUFACTURE

[75] Inventor: Gregory J. Del Corso, Sinking Spring, Pa.

[73] Assignee: CRS Holding, Inc., Wilmington, Del.

[21] Appl. No.: 173,343

[22] Filed: Dec. 23, 1993

[51] Int. Cl.$^6$ .............................. C22C 19/07; B22F 3/14
[52] U.S. Cl. ................... 75/243; 75/244; 75/246; 75/355; 75/950; 419/11; 419/16; 419/48
[58] Field of Search ............................ 75/235, 232, 243, 75/244, 246, 355, 950; 419/11, 16, 48

[56] References Cited

U.S. PATENT DOCUMENTS

| | | | |
|---|---|---|---|
| 3,865,585 | 2/1975 | Rademacher | 75/171 |
| 4,631,082 | 12/1986 | Andrews et al. | 75/235 |
| 4,668,290 | 5/1987 | Wang et al. | 75/235 |
| 5,002,731 | 3/1991 | Crook et al. | 420/440 |

FOREIGN PATENT DOCUMENTS

| | | |
|---|---|---|
| 0213781 | 3/1987 | European Pat. Off. |
| 2000188 | 1/1979 | United Kingdom. |

OTHER PUBLICATIONS

Joseph C. Runkle et al., "A Comparison of the Fatigue Performance of Cast Wrought and HIP P/M Cobalt–Chromium Prosthetic Alloys", Proc. of 1984 Int'l. P/M Conf., MPIF, 1985, vol. 16, pp. 705–725.

A. Aizaz et al., "Properties of 'Stellite'® Alloy No. 21 Made Via Pliable Powder Technology", Proc. of 1984 Int'l P/M Conf., MPIF, 1985, vol. 16, pp. 675–693.

T. Kilner et al., "Nitrogen Strengthening of F75–76 Alloys", The 11th Annual Meeting of the Society for Biomaterials, San Diego, Calif., Apr. 25–28, 1985, p. 91.

H. A. Luckey et al., "Improved Properties of Co–Cr–Mo Alloy by Hot Isostatic Pressing of Powder", 4th Ann. Mtg. Soc. for Biomaterials and the 10th Ann. Int'l. Biomaterials Symposium, Texas, 1978, pp. 71–72.

TECPHY Technical Data Sheet, Cobalt Base Steels (Powder Metallurgy) (Publn. Date Unknown, but not later than Feb. 11, 1992).

"Haynes Stellite" Alloy No. 21, *Alloy Digest*, (May 1953).

"*Cast Cobalt–Chromium–Molybdenum Alloy for Surgical Implant Applications*", ASTM Standard Specification Designation: F 75–87.

"*Thermomechanically Processed Cobalt–Chromium–Molybdenum Alloy for Surgical Implants*", ASTM Standard Specification Designation: F 799–87.

*Haynes Alloys for High Temperature*, Haynes Stellite Div., Union Carbide and Carbon Corp. (1950).

"*Mediosurgical Material Surgical Implants*", French National Standard NF S. 90–402 (Apr. 1983).

K. K. Wang, et al., "The Development Of A New Dispersion Strengthened Vitallium® Alloy for Medical Implants", *Metal Powder Industries Federation, American Powder Metallurgy Institute*, vol. 20, pp. 361–375.

D. J. Levine, "Metallurgical Relationships Of Porous–Coated ASTM F75 Alloys", *Quantitative Characterization and Performance of Porous Implants for Hard Tissue Applications*, pp. 60–73.

T. Kilner, et al., "Static mechanical properties of cast and sinter–annealed cobalt–chromium surgical implants", *J. Mat. Sci.*, vol. 21, No. 4, pp. 1349–1356 (1986).

J-P. Immarigeon, et al., "Microstructural Changes during Isothermal Forging of a Co–Cr–Mo Alloy", *Metallurgical Transactions A*, vol. 15A, Feb. 1984, pp. 339–345.

*Primary Examiner*—Ngoclan Mai
*Attorney, Agent, or Firm*—Dann, Dorfman, Herrell and Skillman

[57] ABSTRACT

A powder metallurgy article formed from a Co—Cr—Mo alloy powder and a method for making the article are disclosed. The Co—Cr—Mo alloy powder contains, in weight percent, about 0.35% max. C, about 1.00% max. Mn, about 1.00% max. Si, about 26.0–30.0% Cr, about 5.0–7.0% Mo, about 3% max. Ni, about 0.25% max. N, about 1.00% max. Fe, about 0.01% max. of oxide forming metals, and the balance is essentially Co. Within their respective weight percent limits C and N are controlled such that they satisfy the relationship:

$$62.866 + 360.93 \times (\%C) + 286.633 \times (\%N) - 682.165 \times (\%C)^2 - 641.702 \times (\%N)^2 \geq 120.$$

18 Claims, No Drawings

CO-CR-MO POWDER METALLURGY ARTICLES AND PROCESS FOR THEIR MANUFACTURE

BACKGROUND OF THE INVENTION

Co—Cr—Mo alloys designated as ASTM F75, "STELLITE" Alloy No. 21, "CARPENTER CCM" and GADS "VITALLIUM" are used in medical devices, particularly surgical implants. Such devices require good wear resistance for their articulating surfaces and high strength to handle the loads imposed during use. The "STELLITE" Alloy No. 21 has been extensively used in implant devices. In the late 1980's, the upper weight percent limit for nickel in ASTM F75 (F75-87) was lowered from 3% to 1% in order to reduce the risk of in vivo allergic reactions to nickel. The lower nickel specification of F75-87 separated the two alloy grades and currently both "STELLITE" Alloy No. 21, containing up to 3% nickel, and ASTM F75-87, containing up to 1% nickel, are used in cast form for medical implant devices.

Cast material suffers from microstructural defects such as porosity and carbide segregation (carbide networking or carbide pooling). Porosity leads to localized corrosion and degradation of mechanical properties of a cast implant. Carbide segregation in a cast alloy is believed to be a cause of corrosion related failure of cast implants. It is known to subject a cast implant to a homogenization heat treatment in order to reduce carbide segregation. Hot isostatic pressing (HIP) of cast parts is used to eliminate porosity resulting from the casting operation.

The purpose of the post-casting thermal treatments is to increase the performance of the implants in use by eliminating local defects in the microstructure. However, such thermal treatments reduce the overall hardness and strength of the material and, thus, adversely affect the wear resistance provided by the alloys. To offset the loss of hardness and strength resulting from a post-casting thermal treatment, an aging treatment can be used to increase the strength of a cast surgical implant that has been homogenized or HIP'd.

Because of the difficulties encountered with cast material, the use of cast and wrought material was pursued. Manufacturing of the F75-87 alloy by standard cast/wrought practices has proven to be difficult because the carbide segregation present in the as-cast ingot makes the material difficult to hot work. In an effort to make the F75-87 alloy easier to hot work without resorting to special techniques, the base F75-87 alloy composition was modified by lowering the carbon content to a nominal 0.05% and adding up to 0.20% nitrogen. The composition of the modified alloy is defined in ASTM F799-87 (F799). The "CARPENTER CCM" alloy is typical of such grades. The reduction in carbon reduces the amount of carbide segregation present in the cast ingot. The addition of nitrogen increases the strength of the alloy and compensates for the loss of strength that would otherwise result from the lower carbon content. The nitrogen-strengthened material is frequently prepared by thermomechanical processing (TMP), a combination of thermal treatment and simultaneous mechanical hot working below the recrystallization temperature, to achieve the higher mechanical properties and hardness specified in ASTM F799 for surgical implants. Typically, TMP is performed at temperatures in the range of 1700–1900F.

TMP requires close control to assure that all of the material possesses the same amount of mechanical working to achieve uniform and reproducible mechanical properties from bar to bar or part to part. This is particularly true during the forging of finished or near-finished products from bar-stock, where several reheats and forging passes are employed to shape the product. The forging practice changes with the product geometry, particularly its thickness. The ability to achieve ASTM F799 properties becomes difficult or impossible depending on the ability to forge the material at the proper temperature to achieve the desired amount of residual stress in the forged part. This means using TMP'd bar-stock that meets ASTM F799 mechanical properties does not guarantee a forger that the forged product he makes will meet the properties specified in ASTM F799. Part-to-part reproducibility is also a concern as is die wear, which increases as lower temperatures are used to "work in" the desired mechanical properties.

Nitrogen, in the form of nitrides, does not retard grain growth as well as carbon in the form of carbides. That characteristic presents a problem in connection with porous coated, i.e., uncemented, implants. Such implants were developed to provide better fixation in the body than cemented implants. To produce a porous coated implant, metal powder or fine wire is sintered onto the alloy substrate. The sintering operation requires heating the article to a high temperature to properly bond the powder to the substrate. Unless special precautions are taken, such a high temperature cycle can cause grain growth, segregation, and microporosity in the substrate material with a resulting loss of corrosion resistance and strength, particularly fatigue strength.

To remedy the grain size problem, a dispersion strengthened version of the "VITALLIUM" alloy (GADS "VITALLIUM") has been developed. As described in U.S. Pat. No. 4,668,290, the GADS "VITALLIUM" alloy contains a dispersion of metal oxides that offset the adverse effects of the sintering process. The GADS "VITALLIUM" alloy can only be produced using powder metallurgy processing as opposed to cast/wrought processing.

The GADS "VITALLIUM" alloy contains a dispersion of relatively hard metal oxide particles which appreciably strengthens the alloy, but can also render it relatively difficult to process. The GADS "VITALLIUM" alloy powder is consolidated and hot worked to produce bar-stock. The finished bar-stock of the alloy may contain small ultrasonic indications resulting from microporosity that forms during hot working of the alloy. Such indications apparently result from the hot working parameters selected (billet temperature or amount of reduction per pass) and/or the difference in plasticity between the matrix material and the dispersed metal oxides. Bar-stock of the GADS "VITALLIUM" alloy has been found to be difficult to cold straighten and the material is known to break on occasion during the cold-straightening process, apparently because of stress intensification resulting from the presence of the metal oxide particles. The limited ability to cold straighten bar forms of the GADS "VITALLIUM" alloy, makes it more difficult and expensive to process the material into finished bar.

The GADS "VITALLIUM" alloy is also difficult to machine because of the dispersed metal oxides. Consequently, this alloy is supplied primarily in forge-bar form. The forge bar can be further hot worked to eliminate any microporosity.

The use of nitrogen as a strengthening agent for porous coated implants is known, as described in T. Kilner et al., *Nitrogen Strengthening of F75-76 Alloys*, Proceedings of the 11th Annual Meeting of the Society for Biometals, Apr. 25–28, 1985. That reference shows that the yield strength of porous coated F75-76 alloy (3.00% max. Ni) can be increased to about 75 ksi by nitriding the alloy. However, the increased yield strength does not meet the 120 ksi minimum yield strength required by ASTM F799. The non-nitrided material has a carbon content of 0.07% and provides a yield strength of about 50 ksi (340 MPa).

Combinations of nitrogen and carbon have also been studied in connection with the ASTM F75 alloy to improve the alloy's ductility as well as its yield and tensile strengths. U.S. Pat. No. 3,865,585 describes an alloy containing up to 0.5% carbon and 0.15 to 0.5% nitrogen. Despite the improvement in ductility reported for that alloy, its yield and tensile strengths do not meet the mechanical requirements of ASTM F799.

Powder metallurgy processing has also been used to produce surgical implants from the "STELLITE 21" and F75-87 alloys. It is generally known that powder metallurgy products possess a more homogeneous microstructure than cast/wrought products. The mechanical properties of the known powder metallurgy products generally meet the requirements of ASTM F75-87 (65 ksi yield strength min.), but do not meet those of ASTM F799 (120 ksi yield strength min.). The known powder metallurgy products can be thermomechanically processed in order to meet the mechanical properties of ASTM F799. The powder metallurgy products can also be subjected to an aging heat treatment to increase the hardness and to improve the mechanical properties such as yield strength. Annealing a powder metallurgy product results in a significant reduction in the strength and hardness of the alloy, such that the powder metallurgy alloy product does not have a hardness of at least 35 HRC, the minimum hardness specified in ASTM F799. A hardness equal to or greater than 35 HRC is desired in the implant industry to achieve the best performance of implant devices during in vivo use.

SUMMARY OF THE INVENTION

The aforementioned problems associated with the cast or cast/wrought products and the known powder metallurgy products are solved to a large degree by preparing Co—Cr—Mo steel articles by a process according to the present invention. In accordance with one aspect of this invention there is provided a method for producing a steel alloy article having a unique combination of strength, hardness, ductility, and corrosion resistance. The process includes the step of preparing a powdered alloy charge consisting essentially of, in weight percent, about 0.35% max. C, about 1.00% max. Mn, about 1.00% max. Si, about 26.0–30.0% Cr, about 5.0–7.0% Mo, about 3% max. Ni, about 0.25% max. N, about 1.00% max. Fe, and the balance is essentially Co. Within their respective weight percent limits C and N are controlled such that they satisfy the relationship:

$$62.866+360.93\times(\%C)+286.633\times(\%N)-682.165\times(\%C)^2-641.702\times(\%N)^2 \geq 120.$$

Furthermore, oxide forming elements such as magnesium, calcium, aluminum, yttrium, lanthanum, titanium, or zirconium are maintained a very low levels, i.e., not more than about 0.01%, in order to avoid the formation of metal-oxide phases that adversely affect the properties of the powder metallurgy article according to the invention.

The powder alloy charge is consolidated at a temperature and pressure selected to produce a substantially fully dense compact. Here and throughout this specification the term "substantially fully dense" means a metal powder compact that has essentially no interconnected porosity. For purposes of the present invention, a substantially fully dense body has a density that is at least about 95% of theoretical density. After consolidation, the compact can be mechanically hot worked to provide a desired product form.

In accordance with another aspect of the present invention, there is provided a substantially fully dense, powder metallurgy article formed from a Co—Cr—Mo alloy powder. The alloy powder consists essentially of, in weight percent, about 0.35% max. C, about 1.00% max. Mn, about 1.00% max. Si, about 26.0–30.0% Cr, about 5.0–7.0% MO, about 3.00% max. Ni, about 0.25% max. N, about 1.0.0% max. Fe, and the balance is essentially Co. Within their respective weight percent limits C and N are controlled such that they satisfy the relationship:

$$62.866+360.93\times(\%C)+286.633\times(\%N)-682.165\times(\%C)^2-641.702\times(\%N)^2 \geq 120.$$

As described above, the alloy powder contains not more than about 0.01% of oxide forming metals.

DETAILED DESCRIPTION

In carrying out the process according to the present invention, an alloy powder charge is prepared, consolidated to substantially full density, and then hot worked to a desired shape or form. The alloy powder has a composition that generally conforms to either ASTM F75-87 or ASTM F799-87. However, the carbon and nitrogen are controlled such that, in the as-hot-worked condition, an article formed from the alloy powder has mechanical properties, i.e., yield and tensile strength, ductility, and hardness, that meet or exceed ASTM F75-87 and ASTM F799-87.

The preferred composition of a powder metallurgy article made in accordance with this invention consists essentially of, in weight percent, about 0.35% max. carbon, about 1.0% max. each of manganese, silicon, and iron, about 26–30% chromium, up to about 3%, preferably up to about 1.0% max., nickel, about 4–7% molybdenum, about 0.25% max. nitrogen, and the balance is essentially cobalt. The powder metallurgy article contains no more than about 0.01% of oxide forming metals in order to avoid the presence of metal oxide phases in the alloy structure. Such metal oxide phases can adversely affect the desired properties of the powder metallurgy article according to this invention.

In preparing the alloy powder charge, the carbon and nitrogen are controlled such that the following relationship is satisfied:

$$62.866+360.93\times(\%C)+286.633\times(\%N)-682.165\times(\%C)^2-641.702\times(\%N)^2 \geq 120.$$

Preferably, the alloy powder contains at least about 0.31% carbon and nitrogen combined. Good results have been obtained with alloy powder containing about 0.19–0.29% carbon and about 0.13–0.25% nitrogen. For best results, the alloy powder contains about 0.25–0.28% carbon and about 0.15–0.20% nitrogen.

The preferred method of making the alloy powder is to melt a heat of alloying materials to provide a molten alloy having approximately the following weight percent composition: 0.35% max. carbon, 1.00% max. manganese, 1.00% max. silicon, 26.0–30.0% chromium, 5.0–7.0% molybdenum, 3% max. nickel, 1.00% max. iron, and the balance essentially cobalt. The preferred melting technique is vacuum induction melting (VIM), although other melting techniques can be used.

During the melting process, the VIM furnace is backfilled with a partial pressure of an inert gas such as argon. Alternatively, the VIM furnace is backfilled with a partial pressure of a cover gas that contains an inert gas and nitrogen gas. In the presence of the inert gas or the cover gas, the molten alloy is superheated to a temperature selected to provide a desired level of nitrogen in the molten alloy. As is known to those skilled in the art, the equilibrium nitrogen solubility in a molten Co—Cr—Mo alloy is inversely related to the temperature of the molten alloy and directly related to the square root of the partial pressure of nitrogen in the melting vessel.

The superheated, molten alloy is atomized with nitrogen gas so as to provide substantially spherical powder particles. The atomized alloy is preferably cooled in an inert atmosphere to prevent excessive nitriding and oxidizing of the powder particles. When cooled, the alloy powder is screened to a desired particle size and then blended.

The screened and blended alloy powder is then filled into a stainless steel canister to a desired fill density and the canister is then closed. The canister is preferably equipped with a fitting that permits the canister to be connected to a vacuum pump. When appropriately connected to a vacuum pump, the powder-filled canister is baked at an elevated temperature while a vacuum is drawn on the interior of the canister. The heating and vacuum treatment is continued for a time sufficient to substantially degas the powder and the interior of the canister.

After the powder-filled canister is degassed, it is sealed and disconnected from the vacuum pump. The powder-filled canister is then consolidated at elevated temperature and pressure for a time sufficient to substantially fully densify the alloy powder. The preferred consolidation technique is hot isostatic pressing (HIP), although other known techniques such as ceramic granular consolidation (CERACON), rapid omnidirectional compaction (ROC) or other fluid die consolidation technique, or hot extrusion can be used.

The powder-filled canister is preferably consolidated at as high a temperature as practical in order to benefit the hot workability of the consolidated alloy powder charge. However, it is preferred that the consolidation temperature does not exceed the incipient melting temperature of the alloy powder.

The consolidated alloy powder is hot worked in a known manner such as by cogging, forging, pressing, or rolling to provide a desired product form. The consolidated alloy powder is preferably hot worked from a temperature of about 2100° F. When desired, the as-hot-worked alloy powder compact can be machined to a final dimension for commercial sale. The canister remnant is removed from the hot-worked billet preferably by machining.

Although either annealed or unannealed material can be used as forging or machining stock, it is preferred that the unannealed material be used because it has a finer grain size. For certain uses that do not require very high strength, the hot-worked alloy powder compact can be annealed. It has been found that an article made in accordance with the process of the present invention provides a hardness greater than about 35 HRC after having been annealed at temperatures up to about 2220° F. The metallurgical advantage of annealed material over as-hot-worked material is that the carbide morphology is more uniform throughout the material. In the annealed material the carbides are uniformly present both within the grains and at the grain boundaries, whereas in the as-hot-worked material, the carbides are predominantly at the grain boundaries. A uniform carbide distribution may be desirable for certain applications.

EXAMPLES

Four nominally 500 lb heats of alloy powder, Examples 1–4, having the weight percent compositions shown in Table I below were produced by vacuum induction melting (VIM) in a VIM capable gas atomization unit. Also shown in Table I is the weight percent composition of similarly prepared, commercially available powder, Heat A, having a composition that conforms to ASTM F75-87.

In melting the example heats, the furnace was initially evacuated to a subatmospheric pressure of about 9μm Hg. During the melting stages for Examples 1 and 2 and Heat A, the VIM furnace was backfilled to a partial pressure of about 20 in Hg with argon gas. During the melting stages of Examples 3 and 4, the VIM furnace was backfilled to a partial pressure of about 20 in Hg with nitrogen gas and then to a partial pressure of about 10 in Hg with argon gas.

When in the molten state, each heat was superheated to a temperature of about 2900° F. After superheating, the molten alloys of Examples 1–4 were tapped and atomized in nitrogen gas to produce substantially spherical powder particles. The molten alloy of Heat A was atomized in argon gas. To prevent excessive nitriding during cooling, the alloy powders of Examples 1–4 were cooled under a partial pressure of argon gas. The alloy powder from each of the five heats was screened to −100 mesh and blended.

TABLE I

|  | Ex. 1 | Ex. 2 | Ex. 3 | Ex. 4 | Heat A |
| --- | --- | --- | --- | --- | --- |
| C | 0.22 | 0.27 | 0.19 | 0.26 | 0.28 |
| Mn | 0.28 | 0.28 | 0.28 | 0.28 | 0.27 |
| Si | 0.68 | 0.64 | 0.66 | 0.65 | 0.65 |
| P | 0.002 | 0.003 | 0.003 | 0.003 | 0.001 |
| S | 0.002 | 0.001 | 0.002 | 0.001 | 0.001 |
| Cr | 28.62 | 28.45 | 28.55 | 28.50 | 28.58 |
| Ni | 0.09 | 0.21 | 0.11 | 0.18 | 0.20 |
| Mo | 6.05 | 6.09 | 6.05 | 6.09 | 6.07 |
| Cu | <0.01 | <0.01 | <0.01 | <0.01 | <0.01 |
| Fe | 0.13 | 0.23 | 0.13 | 0.15 | 0.17 |
| Al | 0.004 | 0.004 | 0.003 | 0.005 | 0.009 |
| N | 0.15 | 0.15 | 0.20 | 0.18 | 0.004 |
| O | 0.0155 | 0.0156 | 0.0151 | 0.0134 | 0.0150 |
| Co | Bal. | Bal. | Bal. | Bal. | Bal. |

Powder from each of Examples 1–4 was air filled into a 4 in rd.×0.065 in wall thickness×96 in long stainless steel canister. The powder from Example 3 was used to fill two canisters hereinafter designated Examples 3A and 3B. The alloy powder was vibrated to maximize the powder fill density in the canisters and then each canister was sealed with a top plate having an evacuation tube. The filled canisters were connected to a vacuum pump and were evacuated to a subatmospheric pressure of less than 1 mm Hg while simultaneously being heated at 250 F. for sufficient time to degas the alloy powder and the canister interior. After the baking and degassing step, the canisters were sealed by crimping and welding the evacuation tubes.

The canisters were then hot isostatically pressed (HIP'd) at 2200 F. for 4 h at a pressure of 15 ksi to substantially full density. The HIP'd canisters were heated to 2075±25 F. in an air furnace and then cogged from 3.6 in rd. to 2.5 in rd. The 2.5 in rd. bars were then cut, reheated to 2075±25 F., and hot rolled to 1.5 in rd. bars with a finish temperature in excess of 1900 F. All of the canisters hot worked well. The powder of comparative Heat A was processed similarly into 2.5 in and 1.5 in round bars.

Samples were taken from all of the 2.5 in rd. bars of Examples 1–4 and from three (3) of the 2.5 in rd. bars of Heat A (AA, AB, and AC), the commercially available ASTM F75 material. Samples were also taken from all of the 1.5 in rd. bars of Examples 1-4 and from five (5) of the 1.5 in rd. bars of Heat A (AD, AE, AF, AG, and AH). Low stress ground room temperature tensile specimens (0.252 in gage diameter) were prepared from each sample and then tested. Shown in Table II are the results of room temperature tensile testing including the 0.2% Offset Yield Strength (0.2% YS) and Ultimate Tensile Strength (UTS) in ksi, the percent elongation (Elong. Percent), the percent reduction in cross-sectional area (RA Percent), and the Rockwell C-scale hardness (Hardness—HRC). Also shown in Table II for easy reference are the minimum mechanical requirements specified in ASTM F799-87.

TABLE II

| Rd. Bar Size | Ex./Ht. No. | 0.2% YS (ksi) | UTS (ksi) | Elong. Percent | RA Percent | Hardness (HRC) |
|---|---|---|---|---|---|---|
| 2.5" | 1 | 142.9 | 192.0 | 15.0 | 16.4 | 45.0 |
| 2.5" | 2 | 136.0 | 190.1 | 18.0 | 19.3 | 44.0 |
| 2.5" | 3A | 142.9 | 192.4 | 15.0 | 16.4 | 46.5 |
| 2.5" | 3B | 146.9 | 197.0 | 15.0 | 17.9 | 43.5 |
| 2.5" | 4 | 146.9 | 200.0 | 18.0 | 19.9 | 42.0 |
| 2.5" | AA | 88.0 | 169.5 | 16.0 | 16.9 | 41.0 |
| 2.5" | AB | 90.0 | 167.4 | 15.0 | 16.5 | 39.5 |
| 2.5" | AC | 92.6 | 178.0 | 15.0 | 18.2 | 42.5 |
| 1.5" | 1 | 143.3 | 192.6 | 21.0 | 21.6 | 45.5 |
| 1.5" | 2 | 151.7 | 197.4 | 15.0 | 18.6 | 46.0 |
| 1.5" | 3A | 139.4 | 189.9 | 19.0 | 20.4 | 43.5 |
| 1.5" | 3B | 144.1 | 191.3 | 20.0 | 20.7 | 43.0 |
| 1.5" | 4 | 147.5 | 195.6 | 18.0 | 19.6 | 44.0 |
| 1.5" | AD | 116.8 | 170.8 | 16.0 | 15.8 | 41.0 |
| 1.5" | AE | 118.2 | 170.5 | 17.0 | 17.4 | 42.0 |
| 1.5" | AF | 110.3 | 171.7 | 22.0 | 21.8 | 38.0 |
| 1.5" | AG | 112.3 | 171.3 | 21.0 | 19.0 | 39.5 |
| 1.5" | AH | 114.9 | 174.0 | 21.0 | 22.1 | 39.0 |
| | ASTM F799 | 120 | 170 | 12 | 12 | 36 |

The data in Table II show that the hot-rolled 2.5 in rd. bars prepared in accordance with the present invention meet the yield and tensile strength requirements of ASTM F799-87 while those prepared from the ASTM F75 alloy powder do not. Furthermore, the 1.5 in rd. bars prepared from the commercial F75 alloy powder do not meet the yield strength requirement of ASTM 799-87, whereas the 1.5 in rd. bars prepared in accordance with the present invention significantly exceed the strength and hardness requirements of ASTM 799-87 while maintaining excellent ductility. The 1.5" rd. hot-rolled bars were then separated into two lots with bars from Examples 1–4 in each lot. One lot of bars was straightened on a Medart straightening machine with the bars in the hot-rolled, unannealed condition. The second lot of bars was annealed at 2220 F. and then gag straightened. The annealing was performed by charging the bars into a furnace that was heated to nominally 1500 F., heating to the annealing temperature, holding at the annealing temperature for 2 h, and then water quenching to room temperature. The unannealed and annealed bars were then turned to remove the remainder of the HIP'g canister. After decanning, the bars were restraightened as required to permit grinding of the turned surfaces. The ground bars were then visually inspected for surface defects and ultrasonically tested for internal defects. The bar surfaces were acceptable and no internal defects were detected.

Samples of the bars were taken after turning for additional testing. A low stress ground tensile specimen and metallographic specimens were prepared from each sample. The results of room temperature tensile testing of the unannealed bars are tabulated in Table IIIA for the unannealed material, including the 0.2% Offset Yield Strength (0.2%YS) and Ultimate Tensile Strength (UTS) in ksi, the percent elongation (Elong. Percent), the percent reduction in cross-sectional area (RA Percent), and the Rockwell C-scale hardness (Hardness —HRC).

TABLE IIIA

| Rd. Bar Size | Example No. | 0.2% YS (ksi) | UTS (ksi) | Elong. Percent | RA Percent | Hardness (HRC) |
|---|---|---|---|---|---|---|
| 1.5" | 1 | 143.3 | 197.6 | 20.0 | 18.6 | 39.3 |
| 1.5" | 2 | 136.7 | 188.2 | 17.0 | 16.5 | 40.0 |
| 1.5" | 3A | 139.5 | 190.5 | 19.0 | 16.2 | 39.1 |
| 1.5" | 3B | 140.4 | 190.4 | 21.0 | 23.2 | 40.9 |
| 1.5" | 4 | 141.1 | 193.8 | 18.0 | 13.0 | 40.1 |

The results of metallographic examination for grain size measurement of the unannealed bars are shown in Table IIIB. The data in Table IIIB include the weight percents of carbon, nitrogen, and carbon-plus-nitrogen and the measured ASTM grain size.

TABLE IIIB

| Example No. | Wt % Carbon | Wt % Nitrogen | Wt % C + N | ASTM Grain Size No. |
|---|---|---|---|---|
| 1 | 0.20 | 0.22 | 0.41 | 12 |
| 2 | 0.21 | 0.16 | 0.36 | 11–12 |
| 3A | 0.27 | 0.15 | 0.42 | 12 |
| 3B | 0.27 | 0.15 | 0.42 | 12 |
| 4 | 0.27 | 0.19 | 0.46 | 12 |

The results of room temperature tensile testing of the annealed bars are tabulated in Table IVA for the unannealed material, including the 0.2% Offset Yield Strength (0.2%YS) and Ultimate Tensile Strength (UTS) in ksi, the percent elongation (Elong. Percent), the percent reduction in cross-sectional area (RA Percent), and the Rockwell C-scale hardness (Hardness —HRC).

TABLE IVA

| Rd. Bar Size | Example No. | 0.2% YS (ksi) | UTS (ksi) | Elong. Percent | RA Percent | Hardness (HRC) |
|---|---|---|---|---|---|---|
| 1.5" | 1 | 100.0 | 187.3 | 35.0 | 28.4 | 34 |
| 1.5" | 2 | 101.7 | 186.6 | 33.0 | 28.1 | 34 |
| 1.5" | 3A | 105.9 | 189.4 | 29.0 | 25.0 | 36 |
| 1.5" | 3B | 103.5 | 187.3 | 29.0 | 24.1 | 36 |
| 1.5" | 4 | 111.3 | 198.0 | 34.0 | 27.6 | 37 |

The results of metallographic examination for grain size measurement of the unannealed bars are shown in Table IVB. The data in Table IVB include the weight percents of carbon, nitrogen, and carbon-plus-nitrogen and the measured ASTM grain size.

TABLE IVB

| Example No. | Wt % Carbon | Wt % Nitrogen | Wt % C + N | ASTM Grain Size No. |
|---|---|---|---|---|
| 1 | 0.20 | 0.22 | 0.41 | 6–8 |
| 2 | 0.21 | 0.16 | 0.36 | 6–7 |
| 3A | 0.27 | 0.15 | 0.42 | 7–9 |
| 3B | 0.27 | 0.15 | 0.42 | 7–9 |
| 4 | 0.27 | 0.19 | 0.46 | 7–9 |

The data in Tables IIIA and IIIB show that unannealed powder metallurgy articles prepared in accordance with the present invention significantly exceed the mechanical requirements of ASTM 799-87 and provide the desired fine grain size. The data in Tables IVA and IVB show that although powder metallurgy articles prepared in accordance with the present invention and annealed at 2220 F. do not meet the yield strength requirement of ASTM 799-87, such articles made from the preferred composition, i.e., Examples 3A, 3B, and 4, do provide a hardness level greater than 35 HRC. Thus, a powder metallurgy article made in accordance with the present invention is suitable for uses that require high hardness in the annealed condition.

In the light of the foregoing description of the invention and the accompanying examples, it can be seen that the present invention provides novel powder metallurgy products and a novel process for producing such articles. Powder metallurgy millform products, such as bar, wire, or sheet, net-shape or near net-shape products, and forgings produced in accordance with this invention meet or exceed the requirements of ASTM 799-87 without the need for thermomechanical processing. Furthermore, powder metallurgy millforms and forgings of the present invention have significantly reduced microporosity compared to the known powder metallurgy products. Because they do not contain a dispersion of metal oxides, powder metallurgy millforms prepared in accordance with this invention provide excellent forgeability and machinability. Surgical implants and other medical devices made from powder metallurgy products of this invention have a more refined and homogeneous structure than cast or cast-and-wrought articles. The improved microstructure of the powder metallurgy articles according to the present invention results in better piece-to-piece consistency of production, as well as better consistency of mechanical properties compared to cast or cast-wrought products.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed.

What is claimed is:

1. A method for producing a Co—Cr—Mo alloy article having a unique combination of strength, hardness, ductility, and corrosion resistance comprising the steps of:

preparing a powdered alloy charge consisting essentially of, in weight percent, about:

|  | % |
| --- | --- |
| Carbon | 0.35 max. |
| Manganese | 1.00 max. |
| Silicon | 1.00 max. |
| Chromium | 26.0–30.0 |
| Molybdenum | 5.0–7.0 |
| Nickel | 3.00 max. |
| Nitrogen | 0.25 max. |
| Iron | 1.00 max. |
| Cobalt | Balance | wherein the amounts of carbon and nitrogen in said alloy satisfy the relationship:

$$62.866+360.93\times(\%C)+286.633\times(\%N)-682.165\times(\%C)^2-641.702\times(\%N)^2 \geq 120;$$

and consolidating said powdered alloy charge at a temperature and pressure selected to produce a substantially fully dense compact.

2. The method of claim 1 wherein the combined amount of carbon and nitrogen is at least about 0.31%.

3. The method of claim 2 wherein said alloy contains at least about 0.19% carbon and at least about 0.13% nitrogen.

4. The method of claim 3 wherein the alloy contains not more than about 0.30% carbon.

5. The method of claim 1 wherein the alloy contains about 1.0% max. nickel.

6. The method of claim 1 comprising the step of mechanically hot working the compact to provide a desired product form.

7. The method of claim 1 wherein the step of preparing the powdered alloy charge comprises the steps of:

melting material in a vessel to form a molten alloy having a composition containing, in weight percent, about:

|  | % |
| --- | --- |
| Carbon | 0.35 max. |
| Manganese | 1.00 max. |
| Silicon | 1.00 max. |
| Chromium | 26.0–30.0 |
| Molybdenum | 5.0–7.0 |
| Nickel | 3.00 max. |
| Iron | 1.00 max. |
| Cobalt | Balance; | atomizing said molten alloy with nitrogen gas to form an alloy powder; and filling a metallic canister with the alloy powder.

8. The method of claim 7 wherein the step of melting the metallic material is performed at subatmospheric pressure.

9. The method of claim 8 wherein the step of melting the metallic material is performed under a partial pressure of an inert gas.

10. The method of claim 8 wherein the step of melting the metallic material is performed under a partial pressure of a cover gas that includes an inert gas and nitrogen gas.

11. The method of claim 7 wherein the step of atomizing the molten alloy comprises the step of cooling the alloy powder in an inert gas.

12. A substantially fully dense, powder metallurgy article, formed from a Co—Cr—Mo alloy powder having a composition in weight percent of about:

|  | % |
| --- | --- |
| Carbon | 0.35 max. |
| Manganese | 1.00 max. |
| Silicon | 1.00 max. |
| Chromium | 26.0-30.0 |
| Molybdenum | 5.0-7.0 |
| Nickel | 3.00 max. |
| Nitrogen | 0.25 max. |
| Iron | 1.00 max. |
| Oxide Forming Metals | 0.01 max. |

| | % |
|---|---|
| Cobalt | Balance | wherein the amounts of carbon and nitrogen in said alloy satisfy the relationship:

$$62.866+360.93\times(\%C)+286.633\times(\%N)-682.165\times(\%C)^2-641.702\times(\%N)^2 \geq 120.$$

13. The powder metallurgy article of claim 12 wherein the combined amount of carbon and nitrogen is at least about 0.31%, 14. The powder metallurgy article of claim 13 wherein said alloy contains at least about 0.19% carbon and at least about 0.13% nitrogen.

15. The powder metallurgy article of claim 14 wherein the alloy contains not more than about 0.30% carbon.

16. The powder metallurgy article of claim 12 wherein the alloy contains about 0.19–0.29% carbon and about 0.13–0.25% nitrogen.

17. The powder metallurgy article of claim 12 wherein the alloy contains about 0.25–0.28% carbon and about 0.15–0.20% nitrogen.

18. The powder metallurgy article of claim 12 wherein the alloy contains about 1.0% max. nickel.

* * * * *